United States Patent [19]
Simon

[11] Patent Number: 5,846,843
[45] Date of Patent: Dec. 8, 1998

[54] SENSOR USING LONG RANGE SURFACE PLASMON RESONANCE WITH DIFFRACTION DOUBLE-GRATING

[75] Inventor: Henry John Simon, Sylvania, Ohio

[73] Assignee: The University of Toledo, Toledo, Ohio

[21] Appl. No.: 751,614

[22] Filed: Nov. 18, 1996

[51] Int. Cl.⁶ .................................................. G01N 33/552
[52] U.S. Cl. .......................... 436/527; 385/12; 385/129; 385/130; 385/131; 422/55; 422/57; 422/82.05; 422/82.11; 435/287.1; 435/287.2; 435/288.7; 435/808; 436/164; 436/518; 436/524; 436/525; 436/531; 436/535; 436/805
[58] Field of Search ................................ 385/12, 129, 130, 385/131; 422/55, 57, 82.05, 82.11; 435/287.1, 287.2, 288.7, 808; 436/164, 518, 524, 525, 527, 531, 535, 805

[56] References Cited

U.S. PATENT DOCUMENTS

| | | | |
|---|---|---|---|
| 4,815,843 | 3/1989 | Tiefenthaler et al. | 356/128 |
| 4,882,288 | 11/1989 | North et al. | 436/525 |
| 4,889,427 | 12/1989 | Van Veen et al. | 356/445 |
| 4,931,384 | 6/1990 | Layton et al. | 435/7 |
| 4,997,278 | 3/1991 | Finlan et al. | 356/128 |
| 5,006,716 | 4/1991 | Hall | 436/172 |
| 5,023,053 | 6/1991 | Finlan | 422/82.05 |
| 5,035,863 | 7/1991 | Finlan et al. | 422/82.05 |
| 5,047,213 | 9/1991 | Finlan et al. | 422/82.11 |
| 5,055,265 | 10/1991 | Finlan | 422/82.05 |
| 5,064,619 | 11/1991 | Finlan | 422/82.05 |
| 5,118,608 | 6/1992 | Layton et al. | 435/7.1 |
| 5,157,537 | 10/1992 | Rosenblatt | 359/245 |
| 5,164,589 | 11/1992 | Sjödin | 250/227.24 |
| 5,210,404 | 5/1993 | Cush et al. | 250/216 |
| 5,242,828 | 9/1993 | Bergström et al. | 435/291 |
| 5,255,075 | 10/1993 | Cush | 356/445 |
| 5,304,465 | 4/1994 | Garland et al. | 435/4 |
| 5,310,686 | 5/1994 | Sawyers et al. | 436/518 |
| 5,313,264 | 5/1994 | Ivarsson et al. | 356/73 |
| 5,327,225 | 7/1994 | Bender et al. | 356/445 |
| 5,341,215 | 8/1994 | Seher | 356/445 |
| 5,351,127 | 9/1994 | King et al. | 356/445 |
| 5,415,842 | 5/1995 | Maule | 422/82.05 |

FOREIGN PATENT DOCUMENTS

WO88/07202  9/1988  United Kingdom .

OTHER PUBLICATIONS

"Attenuated total reflectance from a layered silver grating with coupled surface waves", Zhan Chen & H.J. Simon, Journal of Optical Society of America, B. vol. 5, Jul. 1988, pp. 1396–1400.

*Primary Examiner*—Christopher L. Chin
*Attorney, Agent, or Firm*—Brinks Hofer Gilson & Lione

[57] ABSTRACT

A long range surface plasmon resonance sensor for use in biological, biochemical or chemical testing. The sensor includes a first dielectric medium and a second dielectric medium having an index of refraction approximately matching the first dielectric medium. A double-grating structure is located between the first dielectric medium and the second dielectric medium. A beam of electromagnetic radiation is introduced into the second dielectric medium in a manner which causes long range surface plasmon resonance to occur such that the beam of radiation suffers attenuated total reflection. The characteristics of the resonance dependent upon the reaction between the bonding layer and the targeted bonding molecule are then detected.

20 Claims, 1 Drawing Sheet

SENSOR USING LONG RANGE SURFACE PLASMON RESONANCE WITH DIFFRACTION DOUBLE-GRATING

FIELD OF THE INVENTION

The present invention relates to a sensor having a diffraction double-grating employing long range surface plasmon resonance (LRSP) for use in biological, biochemical and chemical testing for increased sensitivity. More particularly, the present invention relates to an immunosensor having a diffraction double-grating employing long range surface plasmon resonance for use in monitoring the interaction of antibodies with their corresponding antigens.

BACKGROUND OF THE INVENTION

When antibodies are immobilized on a surface the properties of the surface change when a solution containing a corresponding antigen is brought into contact with the surface to allow the antigen to bind with the antibody. The change in the optical properties of the surface can be monitored with a suitable sensor.

The phenomenon of surface plasmon resonance (SPR) can be used to detect minute changes in the refractive index of the surface as the reaction between the antigen and the antibody proceeds. Surface plasmon resonance is the oscillation of free electrons which exists at a metal boundary induced by a time varying electric field. These oscillations are affected by the refractive index of the material adjacent the metal surface and it is this that forms the basis of the sensor mechanism. Surface plasmon resonance may be achieved by using the evanescent wave which is generated when a P-polarized light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299, the entire document of which is incorporated herein by reference.

An object of the present invention is to improve the sensitivity of the basic surface plasmon resonance sensor utilizing the phenomenon of long range surface plasmon resonance. This phenomenon is described in a paper entitled "Attenuated Total Reflectance From a Layered Silver Grating with Coupled Surface Waves" by Zhan Chen and H. J. Simon in Journal of the Optical Society B 5, 1396 (1988), the entire document of which is incorporated herein by reference.

SUMMARY OF THE INVENTION

Briefly, the present invention provides a long range surface plasmon resonance sensor for use in biological, biochemical or chemical testing. The sensor includes a first dielectric medium and a second dielectric medium having an index of refraction approximately matching the first dielectric medium. A double-grating structure is located between the first dielectric medium and the second dielectric medium. A beam of electromagnetic radiation is introduced into the second dielectric medium in a manner which causes long range surface plasmon resonance to occur such that the beam of radiation suffers attenuated total reflection. The characteristics of the resonance dependent upon the reaction between the sample and the sensitive layer are then detected.

In a preferred embodiment, the second dielectric medium includes a first layer of molecules bound to the double-grating structure, a second layer of molecules underlying and attached to the first layer of molecules and a liquid solution containing the molecules to be detected. In a most preferred embodiment, the first layer is a layer of antigen molecules, the second layer is a layer of antibody molecules and the liquid solution is a serum containing antibody proteins.

DESCRIPTION OF THE DRAWINGS

Further features and other objects and advantages of this invention will become clear from the following detailed description made with reference to the drawings in which.

DETAILED DESCRIPTION OF THE PREFERRED EMBODIMENTS

Figure 1:
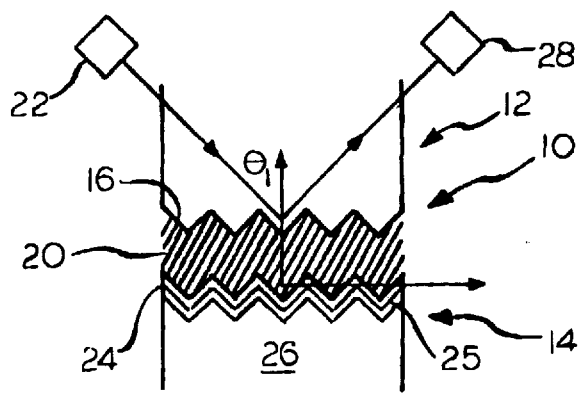
FIG. 1 is a diagram of the optical layer structure in accordance with the present invention to obtain long range surface plasmon resonance.

Referring to the drawings, wherein like reference characters represent like elements, FIG. 1 illustrates a diagrammatic sectional view through the optical layer structure of a sensor 10 to obtain long range surface plasmon resonance.

The sensor 10 includes a first dielectric medium 12 and a second dielectric medium 14. The first dielectric medium 12 is a material in which an electromagnetic wave can be propagated with a minimum dissipation of power. In a preferred embodiment, the first dielectric medium 12 is a high refractive index glass or plastic material transparent to electromagnetic radiation. The refractive index of the first dielectric medium 12 must be approximately the same as the effective refractive index of the second dielectric medium 14. In a preferred embodiment, the refractive index of the first dielectric medium 12 is about 1.4 or that of an aqueous solution. Formed in the bottom surface of the first dielectric medium 12 is a grating surface 16. The grating surface 16 may be an assembly of narrow grooves having inclined sidewalls. A preferred embodiment of the grating surface 16 would be in the form of a compact disk as well known in the art.

Formed on the bottom surface of the first dielectric medium 12 is a thin metal film of uniform thickness. The metal film must be sufficiently thin to permit simultaneous coupling of surface plasmons at the top and bottom interfaces of the grating, i.e., permit excitation of surface waves on both sides of the thin metal film. In a preferred embodiment, for a silver metal film the thickness of the metal film must be between 15–25 nm, and most preferably no more than about 20 nm. It will be appreciated, that a metal film of no more than about 15–25 nm is substantially thinner than heretofore known metal films of 50 nm or more, typical of single boundary surface plasmons. The thinner metal film ensures excitation of surface waves on both sides of the metallic layer in contrast to heretofore known single boundary surface plasmons and therefor facilitates increased sensitivity of the sensor. It will be further appreciated that the metal film thickness in accordance with the present invention of whatever type of metal will always be at least a factor of two thinner than heretofore metal film thicknesses for single boundary surface plasmons.

The metal film replicates the contour of the grating surface 16 within the first dielectric medium 12.

Consequently, both surfaces of the metal film replicate the grating surface 16 in the first dielectric medium 12 thereby producing a double-grating structure 20. The thin metal film may be silver, gold or aluminum and the like and deposited on the bottom surface of the first dielectric medium 12 by evaporation or sputtering as well known in the art. The arrangement of the double-grating structure 20 interacts with the electromagnetic radiation from a source 22 as further described herein thereby producing excitation of the long-range surface plasmon resonance.

Adjacent the bottom surface of the double-grating structure 20 is a second dielectric medium 14. The second dielectric medium 14 comprises a first organic layer 24, a second organic layer 25 underlying and attached to the first organic layer and a liquid solution 26. In a preferred embodiment, the first organic layer 24 may be an antigen protein and the second organic layer 25 may be the antibody protein which bonds to the antigen. The liquid solution 26 may be a sample such as a serum containing antibody proteins to be tested. By means of a coupling technique such as is known in biotechnology, ligands in the first organic layer 24 are bound to the double-grating structure 20 and serve to interact with specific molecules present in the liquid solution 26. The antigens are bound by the first organic layer 24 as a macromolecular layer of uniform thickness. It will be appreciated that the invention depends on the determination of the change in optical properties, transmission or reflection characteristics, of the double-grating structure caused by the attachment of the ligands in the first organic layer 24 to the specific biomolecules to be assayed which forms the second organic antibody layer 25. The ligands may, for example, be bifunctional or polyfunctional molecules consisting of at least one portion of an antigen complimentary to an antibody that is to be detected. As a result of this functionalization, the sensor 10 may be selectively designed for detection of specific molecules of interest. For example, the first organic layer 24 may be varied to interact with specific molecules present in the liquid solution 26.

A source 22 of radiation and a detector 28 complete the assembly. The radiation source 22 produces a collimated input beam of electromagnetic radiation. The frequency of the radiation must be such as to result in the generation of surface plasmon waves and in practice will be within or near the visible region. Suitable sources include a helium neon laser or an infrared diode laser, but an ordinary light source, with suitable filters and collimators, could be used. Electromagnetic radiation from the source 22 is transmitted through the transparent first dielectric medium 12 to be internally reflected at the interface of the double-grating structure 20 and second dielectric medium 14. The reflected radiation passes out through the first dielectric medium 12 and to the detector 28. The detector 28 may be of most any suitable design well known in the art. For a more detailed discussion of a detector 28, reference is made to U.S. Pat. No. 5,313,264, incorporated herein by reference. The effective refractive properties of the second dielectric medium 14 change when an additional second organic layer 25 of antibody protein attaches to the first organic layer 24 of antigen protein. The latter layer containing antibody proteins is only present during the test and reacts with the first organic layer 24 to alter the refractive index of the first organic layer 24 and therefore the second dielectric medium 14 to thus effect the surface plasmon resonance. As the angle of incidence of the monochromatic light $\Theta_1$ is varied, there is an angle at which the phenomenon of surface plasma is observed manifesting itself as a sharp attenuation in the strength of the internally reflected beam. It is found that there is a sharp dip in reflectivity at an angle $\Theta_1$ whose value depends upon the index of refraction of the composite second dielectric medium 14. Consequently, the angular position of the dip and its angular width are strongly dependent upon the amount of antigens attached to the layer of antibodies thereby providing a quantitative measure of the antibodies absorbed from the sample.

Figure 2:
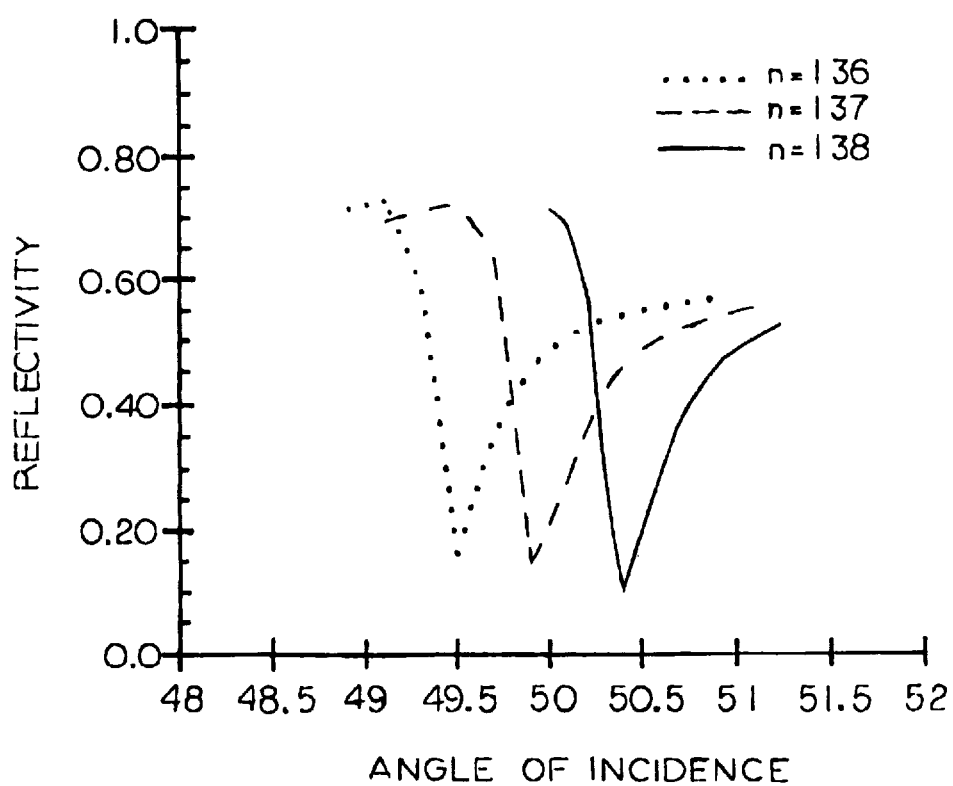
FIG. 2 illustrates the results obtained with an article of the type illustrated in FIG. 1 wherein the x-axis represents the Reflectivity and the y-axis represents the Angle of Incidence.

FIG. 2 is a plot of the reflectivity of a sample against the angle of incidence of the monochromatic, polarized light source over a small angular range. As the antibody is captured out of the solution 26 by the first organic antibody layer 24 the effective index of the second dielectric medium 14 changes slightly. This small change in refractive index alters the angular position of the reflectivity minimum. This feature is shown in FIG. 2 for three different values of effective index of refraction. For a change of index of less than 1% the angular resonance shifts by a 0.5°. Since it is relatively easy to detect shifts of 0.1°, this method is extremely sensitive to the growth of even a monolayer of antibody molecules. This level of sensitivity is a unique characteristic of the long range surface plasmon mode. Further, the sensitivity may be used to estimate changes corresponding to an increase in the average thickness of the antibody layer of around 1 nanometer (nm). It can be calculated that the ATR signal increases by a factor of approximately 5 due to the growth of a few monolayers of 2 nm thickness.

It will be appreciated that the invention is also applicable to other chemical, biochemical or biological species, for example ionic species. The invention may be used for example to determine the metal ion content of a sample. The organic layer may be, for example, a chelating chemical or enzyme or a chelating organism which constitutes a specific binding partner for the ligand or ion which is to be measured.

The patents, patent applications and documents herein are hereby incorporated by reference.

Having described presently preferred embodiments of the invention, it may be otherwise embodied within the scope of the following claims.

What is claimed is:

1. A long range surface plasmon resonance sensor for detecting molecules in a liquid solution comprising:

a first dielectric medium;

a second dielectric medium having an effective index of refraction approximately matching said first dielectric medium;

a double-grating structure between said first dielectric medium and said second dielectric medium;

the second dielectric medium including,
a first organic layer of molecules bound to said double-grating structure specific for said molecules that are to be detected, means for introducing into the first dielectric medium a beam of electromagnetic radiation in a manner which causes long range surface plasmon resonance to occur whereby said beam of radiation suffers attenuated total reflection; and a detector for detecting the attenuated total reflectance of the long range surface plasmon resonance as a function of the formation of a second organic layer of molecules on said first organic layer as the molecules in the liquid solution bind to the molecules of the first organic layer.

2. The long range surface plasmon resonance sensor of claim 1 wherein said first organic layer is a layer of antigen molecules and said second organic layer is a layer of antibody molecules.

3. The long range surface plasmon resonance sensor of claim 2 wherein said first dielectric medium is a material in which an electromagnetic wave can be propagated with a minimum dissipation of power.

4. The long range surface plasmon resonance sensor of claim 2 in which said first dielectric medium is a high refractive index glass or plastic material transparent to electromagnetic radiation.

5. The long range surface plasmon resonance sensor of claim 2 in which the refractive index of said first dielectric medium is about 1.4.

6. The long range surface plasmon resonance sensor of claim 2 in which the refractive index of said first dielectric medium matches that of the liquid solution containing the molecules to be detected.

7. The long range surface plasmon resonance sensor of claim 1 in which a grating surface is formed in the bottom surface of said first dielectric medium.

8. The long range surface plasmon resonance sensor of claim 1 in which said double-grating structure is an assembly of narrow grooves having inclined sidewalls.

9. The long range surface plasmon resonance sensor of claim 1 in which said double-grating structure is in the form of a compact disk.

10. The long range surface plasmon resonance sensor of claim 1 in which said double-grating structure is a metal film of uniform thickness.

11. The long range surface plasmon resonance sensor of claim 1 in which said double-grating structure is a metal film no greater than about 20 nm thick.

12. The long range surface plasmon resonance sensor of claim 11 in which said metal film is selected from the group consisting of silver, gold and aluminum.

13. The long range surface plasmon resonance sensor of claim 1 in which said liquid solution is a serum containing antibody proteins.

14. The long range surface plasmon sensor of claim 2 wherein said antigen molecules of said first organic layer are a macromolecular layer of uniform thickness.

15. The long range surface plasmon resonance sensor of claim 2 wherein the attenuated total reflectance of the long range surface plasmon resonance are caused by attachment of ligands in said first organic layer to said second organic layer.

16. The long range surface plasmon resonance sensor of claim 15 wherein the ligands are bifunctional or polyfunctional molecules consisting of at least one portion of an antigen complimentary to an antibody of said second organic layer.

17. The long range surface plasmon resonance sensor or claim 16 wherein the radiation source produces a collimated input beam of electromagnetic radiation having a frequency to generate surface plasmon waves.

18. A long range surface plasmon resonance sensor for detecting molecules in a liquid solution comprising:
a first dielectric medium;
a second dielectric medium having an effective index of refraction approximately matching said first dielectric medium;
a double-grating structure including a metal film no greater than about 20 nm thick between said first dielectric medium and said second dielectric medium;
the second dielectric medium including,
a first organic layer of molecules bound to the metal film specific for said molecules that are to be detected,
means for introducing into the first dielectric medium a beam of electromagnetic radiation in a manner which causes long range surface plasmon resonance to occur whereby said beam of radiation suffers attenuated total reflection; and
a detector for detecting the attenuated total reflectance of the long range surface plasmon resonance as a function of the formation of a second organic layer of molecules on said first organic layer as the molecules in the liquid solution bind to the molecules of the first organic layer.

19. The long range surface plasmon resonance sensor of claim 18 in which said first dielectric medium is a high refractive index glass or plastic material transparent to electromagnetic radiation.

20. A long range surface plasmon resonance sensor for detecting molecules in a liquid solution comprising:
a first dielectric medium;
a second dielectric medium having an effective index of refraction approximately matching said first dielectric medium;
said second dielectric medium including,
a first organic layer of molecules specific for said molecules that are to be detected,
a double-grating structure including a metal film no greater than about 20 nm thick between said first dielectric medium and said second dielectric medium;
means for introducing into the first dielectric medium a beam of electromagnetic radiation in a manner which causes long range surface plasmon resonance to occur whereby said beam of radiation suffers attentuated total reflection; and
a detector for detecting the attenuated total reflectance of the long range surface plasmon resonance as a function of the formation of a second organic layer of molecules on said first organic layer as the molecules in the liquid solution bind to the molecules of the first organic layer.

* * * * *